(12) United States Patent
Trainoff

(10) Patent No.: US 10,369,600 B2
(45) Date of Patent: Aug. 6, 2019

(54) METHOD AND APPARATUS TO CONTROL SAMPLE CARRYOVER IN ANALYTICAL INSTRUMENTS

(71) Applicant: Wyatt Technology Corporation, Santa Barbara, CA (US)

(72) Inventor: Steven P. Trainoff, Goleta, CA (US)

(73) Assignee: WYATT TECHNOLOGY CORPORATION, Goleta, CA (US)

( * ) Notice: Subject to any disclaimer, the term of this patent is extended or adjusted under 35 U.S.C. 154(b) by 178 days.

(21) Appl. No.: 14/898,246

(22) PCT Filed: Jul. 2, 2014

(86) PCT No.: PCT/US2014/045200
§ 371 (c)(1),
(2) Date: Dec. 14, 2015

(87) PCT Pub. No.: WO2015/003037
PCT Pub. Date: Jan. 8, 2015

(65) Prior Publication Data
US 2016/0129485 A1 May 12, 2016

Related U.S. Application Data

(60) Provisional application No. 61/842,891, filed on Jul. 3, 2013.

(51) Int. Cl.
*B08B 9/032* (2006.01)
*G01N 21/11* (2006.01)
(Continued)

(52) U.S. Cl.
CPC ............ *B08B 9/0321* (2013.01); *G01N 21/11* (2013.01); *G01N 27/44721* (2013.01); *G01N 2021/0389* (2013.01)

(58) Field of Classification Search
CPC .................. B08B 9/0321; G01N 21/05; G01N 2021/0346; G01N 27/44721; G01N 21/15; G01N 35/1095
(Continued)

(56) References Cited

U.S. PATENT DOCUMENTS 3,177,706 A * 4/1965 Shuman ................. G01N 21/05
116/276
3,556,538 A * 1/1971 Muller ................... F16J 15/342
277/361
(Continued)

FOREIGN PATENT DOCUMENTS

DE    10 2009 024 048 B3    8/2010
JP              S60137353 U    9/1985
JP              2005127476 A    5/2005

*Primary Examiner* — David G Cormier
*Assistant Examiner* — Thomas Bucci
(74) *Attorney, Agent, or Firm* — Leonard T. Guzman

(57) ABSTRACT

A method and apparatus are disclosed which enable the reduction of sample carryover in the measurement cell of an analytical instrument. A sample cell is defined as a region sealed within a first o-ring. Located outside of said sample region is another o-ring which seals and defines a seal wash region as the region between the first and second o-ring. After the fluid sample is injected into the measurement cell a pressure is applied to the seal wash region, forcing the first o-ring to the innermost extent of the groove in which it sits, expelling any trapped solvent and removing from the measurement cell a significant dead volume while the cell is flushed and prepared for a new sample and corresponding measurement.

3 Claims, 7 Drawing Sheets

(51) Int. Cl.
   *G01N 27/447* (2006.01)
   *G01N 21/03* (2006.01)
(58) Field of Classification Search
   USPC ..... 134/113, 22.12; 356/246, 440, 436, 410, 356/344, 36, 244; 277/361, 369, 388, 277/400, 431, 927, 345; 250/576, 288, 250/441.11; 604/256
   See application file for complete search history.

(56) References Cited

U.S. PATENT DOCUMENTS

| | | | | |
|---|---|---|---|---|
| 3,795,450 A * | 3/1974 | Munk | G01N 21/05 | 356/246 |
| 3,813,103 A * | 5/1974 | Wiese | F16J 15/3412 | 277/361 |
| 3,886,364 A * | 5/1975 | Walker | G01N 21/0317 | 250/343 |
| 4,094,196 A * | 6/1978 | Friswell | G01N 30/24 | 73/864.21 |
| 4,095,806 A * | 6/1978 | Dempsey | F16J 15/3464 | 277/388 |
| 4,127,330 A * | 11/1978 | Knoche | G01N 21/272 | 356/246 |
| 4,130,287 A * | 12/1978 | Ritzie | F16J 15/36 | 277/361 |
| 4,192,519 A * | 3/1980 | Buggele | F16J 15/028 | 277/638 |
| 4,242,909 A * | 1/1981 | Gundelfinger | G01N 30/24 | 73/864.21 |
| 4,411,575 A * | 10/1983 | Miller | H01J 37/18 | 206/524.1 |
| 4,531,404 A * | 7/1985 | Phelps | G01N 15/0806 | 277/614 |
| 4,588,893 A * | 5/1986 | Vidrine | G01N 21/05 | 250/343 |
| 4,805,443 A * | 2/1989 | Schroeder | G01N 15/0806 | 220/303 |
| 4,889,319 A * | 12/1989 | Phillips | C30B 23/02 | 251/368 |
| 4,988,155 A * | 1/1991 | Harner | B08B 3/04 | 250/227.11 |
| 5,003,174 A * | 3/1991 | Datwyler | G01N 21/05 | 250/343 |
| 5,074,663 A * | 12/1991 | Winterton | G01N 21/552 | 340/605 |
| 5,076,589 A * | 12/1991 | Marsi | F16J 15/006 | 277/319 |
| 5,114,161 A * | 5/1992 | Sgourakes | F16J 15/3204 | 277/500 |
| 5,120,129 A * | 6/1992 | Farquharson | G01N 21/05 | 250/576 |
| 5,249,812 A * | 10/1993 | Volden | F16J 15/162 | 277/361 |
| 5,404,217 A * | 4/1995 | Janik | G01N 15/1404 | 250/576 |
| 5,452,082 A * | 9/1995 | Sanger | G01N 21/05 | 356/246 |
| 5,528,923 A * | 6/1996 | Ledez | G01N 7/14 | 73/19.02 |
| 5,529,315 A * | 6/1996 | Borrino | F16J 15/004 | 277/352 |
| 5,530,540 A * | 6/1996 | Wyatt | G01N 21/05 | 356/246 |
| 5,840,253 A * | 11/1998 | Chase | B04B 5/0407 | 422/63 |
| 5,901,965 A * | 5/1999 | Ringer | F16J 15/363 | 277/361 |
| 5,986,756 A * | 11/1999 | Slater | G01N 21/31 | 250/458.1 |
| 6,188,813 B1 * | 2/2001 | Dourdeville | G01N 21/05 | 250/227.11 |
| 6,224,060 B1 * | 5/2001 | Parker | F16J 15/3448 | 277/348 |
| 6,426,794 B1 * | 7/2002 | Trainoff | G01N 21/05 | 356/246 |
| 6,741,411 B2 * | 5/2004 | Isbert | G01N 21/01 | 116/276 |
| 6,789,804 B2 * | 9/2004 | Wilhelm | F16J 15/38 | 277/345 |
| 6,972,568 B2 * | 12/2005 | Haner | G01R 33/307 | 324/321 |
| 7,259,840 B1 * | 8/2007 | Gerner | G01N 21/05 | 356/36 |
| 7,298,472 B2 * | 11/2007 | Gerner | G01N 21/05 | 356/246 |
| 7,905,493 B2 * | 3/2011 | Hobmeyr | F04D 29/122 | 277/361 |
| 7,973,923 B2 * | 7/2011 | Wynn | F16L 41/03 | 356/246 |
| 8,173,068 B2 * | 5/2012 | Loeffler | B01L 3/502 | 422/501 |
| 8,427,638 B2 * | 4/2013 | Atkinson | E21B 47/011 | 356/241.1 |
| 8,770,589 B2 * | 7/2014 | Hashimoto | F16J 15/3404 | 277/358 |
| 8,829,469 B2 * | 9/2014 | Damiano, Jr. | H01J 37/20 | 250/440.11 |
| 9,207,165 B2 * | 12/2015 | Zhang | G01N 21/03 | |
| 9,554,968 B2 * | 1/2017 | Weikart | A61J 1/00 | |
| 9,764,093 B2 * | 9/2017 | Weikart | A61M 5/3129 | |
| 2002/0060430 A1 * | 5/2002 | Takigahira | F16J 15/3484 | 277/361 |
| 2002/0085959 A1 * | 7/2002 | Carey | B01L 3/508 | 422/400 |
| 2003/0143115 A1 * | 7/2003 | Tanimoto | G01N 1/44 | 422/68.1 |
| 2004/0080744 A1 * | 4/2004 | Hobbs | B01L 3/502715 | 356/246 |
| 2006/0263269 A1 * | 11/2006 | Morozov | B01L 3/502715 | 422/400 |
| 2006/0284108 A1 * | 12/2006 | Buijsse | H01J 37/18 | 250/441.11 |
| 2007/0144274 A1 * | 6/2007 | Gibson | G01N 1/2035 | 73/863.02 |
| 2009/0134582 A1 * | 5/2009 | Murray | F04D 29/167 | 277/361 |
| 2009/0289450 A1 * | 11/2009 | Bluhm | F16D 25/0638 | 285/101 |
| 2010/0166609 A1 * | 7/2010 | Hagiwara | B01L 3/502707 | 422/68.1 |
| 2010/0294049 A1 * | 11/2010 | Kelley | G01N 1/28 | 73/864.83 |
| 2010/0298738 A1 * | 11/2010 | Felts | B05D 1/62 | 600/576 |
| 2011/0057393 A1 * | 3/2011 | van den Boom | F16J 15/062 | 277/312 |
| 2011/0101617 A1 * | 5/2011 | Suefuji | F16J 15/3484 | 277/361 |
| 2011/0141465 A1 * | 6/2011 | Jeannotte | G01N 21/05 | 356/246 |
| 2011/0143365 A1 * | 6/2011 | Buchanan | B01L 3/5029 | 435/7.1 |
| 2012/0025473 A1 * | 2/2012 | Takahashi | F16J 15/3484 | 277/361 |
| 2012/0123345 A1 * | 5/2012 | Felts | A61M 5/3129 | 604/187 |
| 2013/0041241 A1 * | 2/2013 | Felts | C23C 16/045 | 600/364 |
| 2013/0264476 A1 * | 10/2013 | Damiano, Jr. | H01J 37/20 | 250/307 |
| 2013/0312501 A1 * | 11/2013 | Dewey | B01D 29/01 | 73/61.56 |
| 2015/0126941 A1 * | 5/2015 | Felts | A61M 3/0262 | 604/230 |

\* cited by examiner

METHOD AND APPARATUS TO CONTROL SAMPLE CARRYOVER IN ANALYTICAL INSTRUMENTS

BACKGROUND

A common problem associated with liquid sample analytical measurement instruments is the carryover of an injected sample from run-to-run. Whenever two samples are injected sequentially, there is always some trace amount of the first injected sample left in the cell when a second injected sample is measured. Any number of analytical instruments may suffer from this sample carryover, among these are instruments to measure light scattering, refractive index, ultraviolet absorption, viscosity, and electrophoretic mobility. Of particular interest to the present invention is the field of electrophoretic mobility measurements, such as those discussed by Hsieh and Trainoff in U.S. Pat. No. 8,441,638 issued May 14, 2013 and incorporated herein by reference. Various techniques have been used to mitigate the problem of sample carryover. The most simple and commonly used methods to overcome this contamination problem include flushing a large volume of cleaning fluid between sample injections and injecting large amounts of the samples to insure that the cell is overfilled many times such that the majority of the previously injected sample is flushed from the measurement chamber prior to the measurement of the incoming sample. However this is often only marginally effective as measurement cells often include complicated internal geometries with regions that are poorly connected to the main volume of the measurement cell such that it is easy to push sample into these regions but difficult to flush the sample out again. These processes can also waste time and valuable sample and frequently produce excess waste.

One of the most problematic geometries contained within analytical instruments that give rise to sample carryover issues are o-ring grooves. O-rings are commonly used in measurement cells because they are effective, inexpensive, durable and reliable. Moreover a cell built with o-ring seals can generally be disassembled for cleaning and to replace worn or damaged components. O-rings, however, are notorious for enabling the trapping of sample. Consider the uncompressed standard face seal o-ring groove design as shown in FIG. 1. In a standard face seal design, the top plate 101, in this case a disc shaped window, is pressed directly against the manifold surface 102 which contains the groove 103 with no gap between the manifold surface 102 and top plate 101 after compression. The vertical extent of the groove is smaller, typically by 15%, than the diameter of the o-ring 104. As the o-ring 104 is compressed, it deforms and spreads laterally within the groove 103, which is purposefully oversized. The horizontal extent of the groove 103 is typically 1.5× the o-ring diameter, although the width and compression can be optimized for particular applications. The extra volume within the groove 103 is present to compensate for worst-case tolerances of the o-ring, groove machining, chemical swelling of the o-ring material, and differential thermal expansion of the o-ring material and the groove over its operational temperature range. An o-ring designer is forced to leave a substantial extra gap in the groove 103 so that the designed measurement cell does not leak given worst-case tolerances. This gap acts as a carryover reservoir, or dead volume, for any fluid entering the cell, and since the window 101 is pressed directly against the manifold top surface 102, once sample is pushed into this space, it is very difficult to remove. When the seal is pressurized, the o-ring stretches and is forced to the outside edge of the groove, causing the interior gap to fill with fluid. When the seal is depressurized, friction can hold the o-ring in its stretched configuration and the fluid trapped in the seal remains. Given a static load, the only means by which the trapped sample may exit the groove is by diffusion, which is a slow process. An objective of the present invention is to enable a more rapid method than simple diffusion to drastically reduce or completely eliminate carryover in a measurement cell from one sample injection to the next.

Since the interior of the measurement cell is pressurized relative to the environment, the design rules teach that the most reliable seal is formed when the o-ring is pressed against the outside wall 105 of the groove 103, to minimize stretching, and the corresponding reduction in seal compression that results. Nevertheless, one might be tempted to address the carryover problem by designing the o-ring groove 103 so that the ring hugs the inner wall 106, making sure that the dead volume is outside the sample space. This works so long as the pressurization of the cell interior that invariably accompanies filling the cell is small enough that the o-ring's tensile strength, coupled with friction between the o-ring and the sealing surfaces, is sufficient to keep the o-ring in place. However, since o-rings are usually made of compliant rubber, this is rarely sufficient. Moreover as the o-ring ages, repeated pressurizations will cause it to creep to the outside of the groove and friction will hold it in place. At this point the advantages of an inner wall hugging o-ring design are overcome because we once again have the dead volume in the interior of the cell, and in addition, now we have a stretched seal with reduced compression.

As discussed above, some analytical instruments may be engineered to incorporate optimized groove designs which minimize the groove width, using as input parameters: the o-ring material, the expected temperature range of operation, material tolerances, and chemical swell. At extreme tolerances, these grooves may have zero dead volume. However, while these "optimized" systems may enable a decrease of groove volume, and thus less dead volume, if any of the tolerances is exceeded, the system risks a catastrophic failure such as leakage or window breakage. It is an objective of the present invention to enable a means by which carryover may be minimized or eliminated in systems containing o-ring grooves so as to allow for significant non-idealities, including systems wherein the o-ring groove comprises a significant dead volume.

A BRIEF DESCRIPTION OF THE INVENTION

The present invention makes use of a multiple o-ring system in an analytical instrument. Fluidic pressure is applied to a region of the instrument not in contact with the sample to be analyzed. This pressure affects the position and shape of the o-ring which is in fluid contact with the sample causing it to push out sample trapped in the inner portion of the o-ring groove.

A BRIEF DESCRIPTION OF THE DRAWINGS

Figure 6:
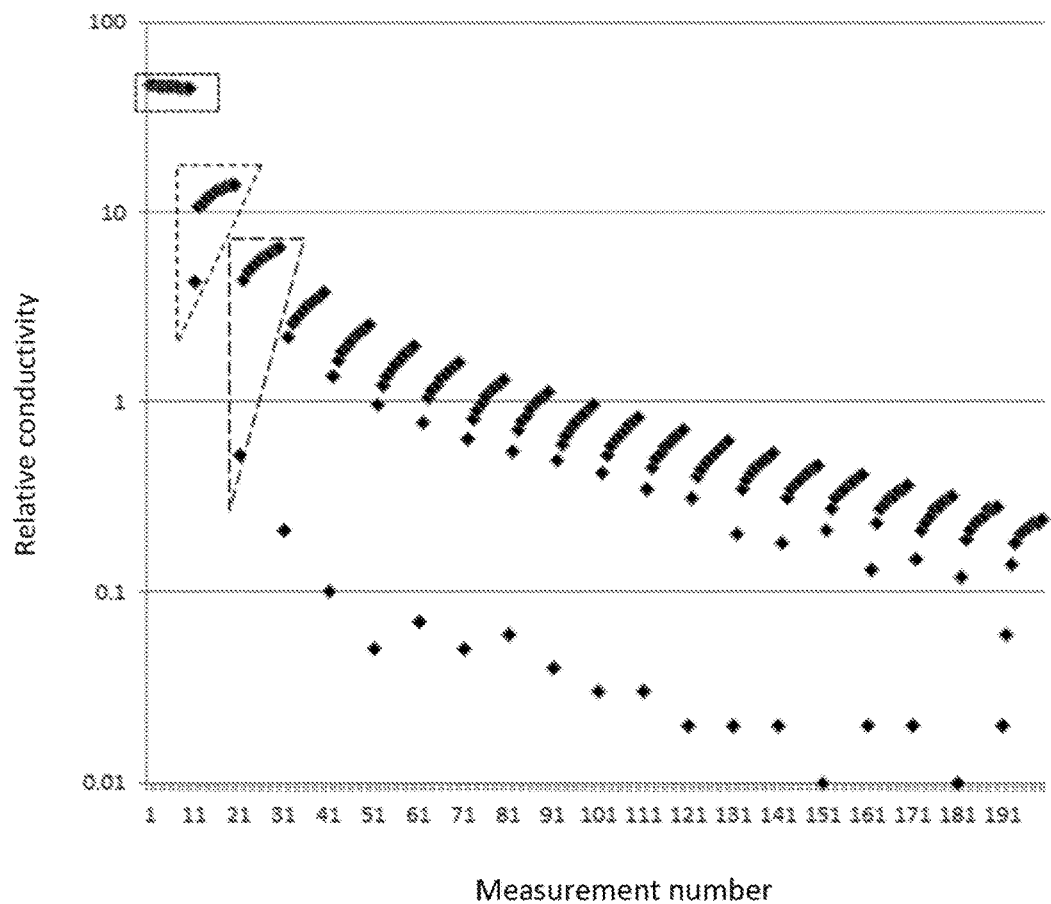

FIG. 6 shows conductivity data collected in a conventional flow through measurement cell of an electrophoretic mobility measurement instrument. An initial high salt concentration is injected and measured ten times, followed by a period of flushing and 10 more measurements. The flush and measure procedure is repeated several more times.

Figure 7:
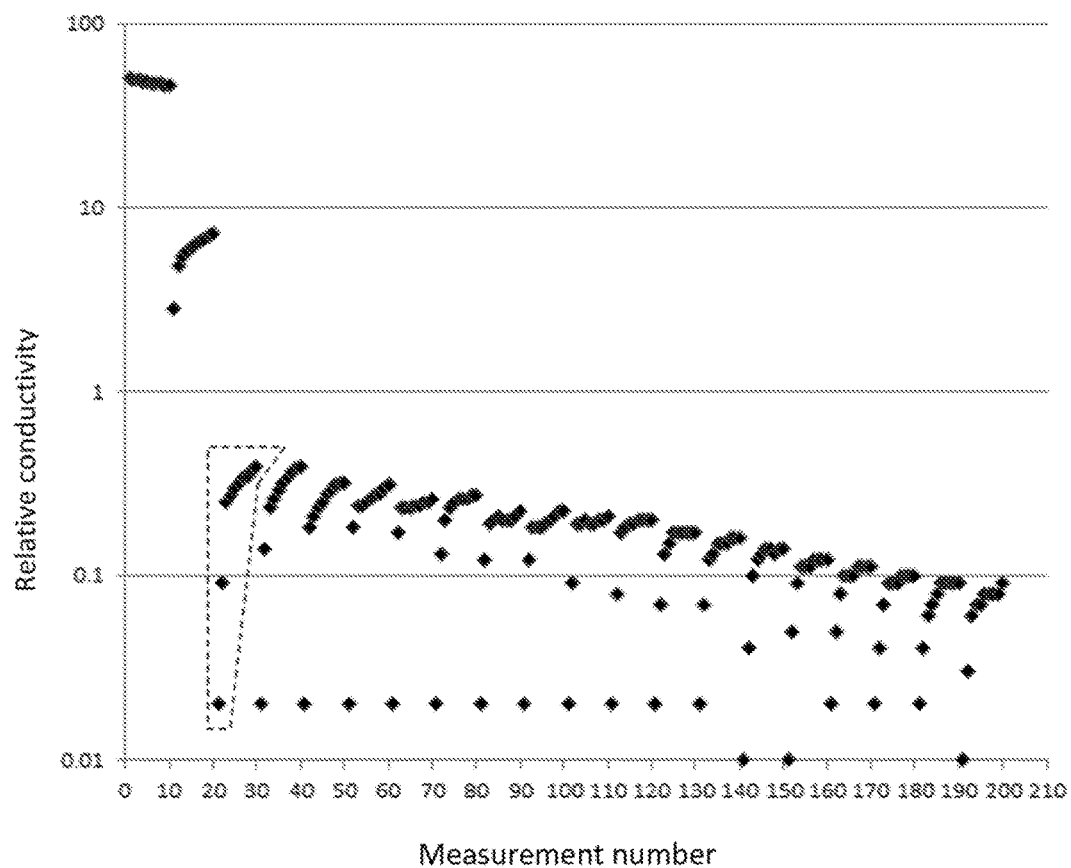

FIG. 7 shows similar conductivity data as collected and displayed in FIG. 6, however this data was generated with a measurement cell and method according to the present invention, with each flushing stage accompanied by four alternating pressure pulses enabling wiping of the sealing surfaces of the inner measurement chamber.

A DETAILED DESCRIPTION OF THE INVENTION

One method of speeding the process of removing sample trapped in the o-ring groove is to exploit the o-ring distortion that occurs when the cell is pressurized. Repeated pressurizing and depressurizing will force some fluid into and out of the dead volume, which will then be flushed out of the measurement cell. The present invention utilizes this process in part, but adds a further pressurization step which significantly improves the rate at which trapped sample may be removed from the measurement cell.

Figure 1:
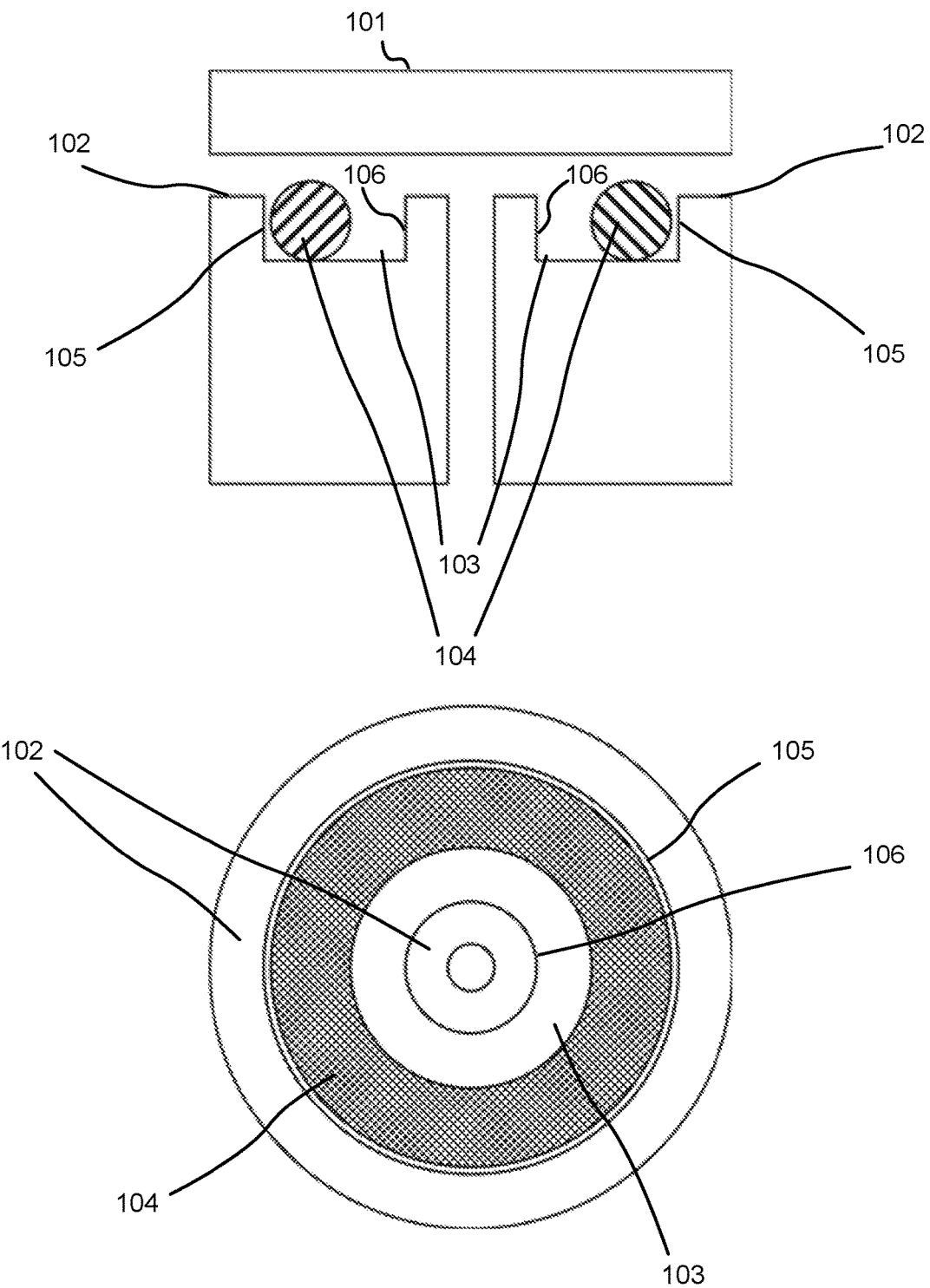
FIG. 1 shows a standard face seal o-ring groove design.
Figure 2:
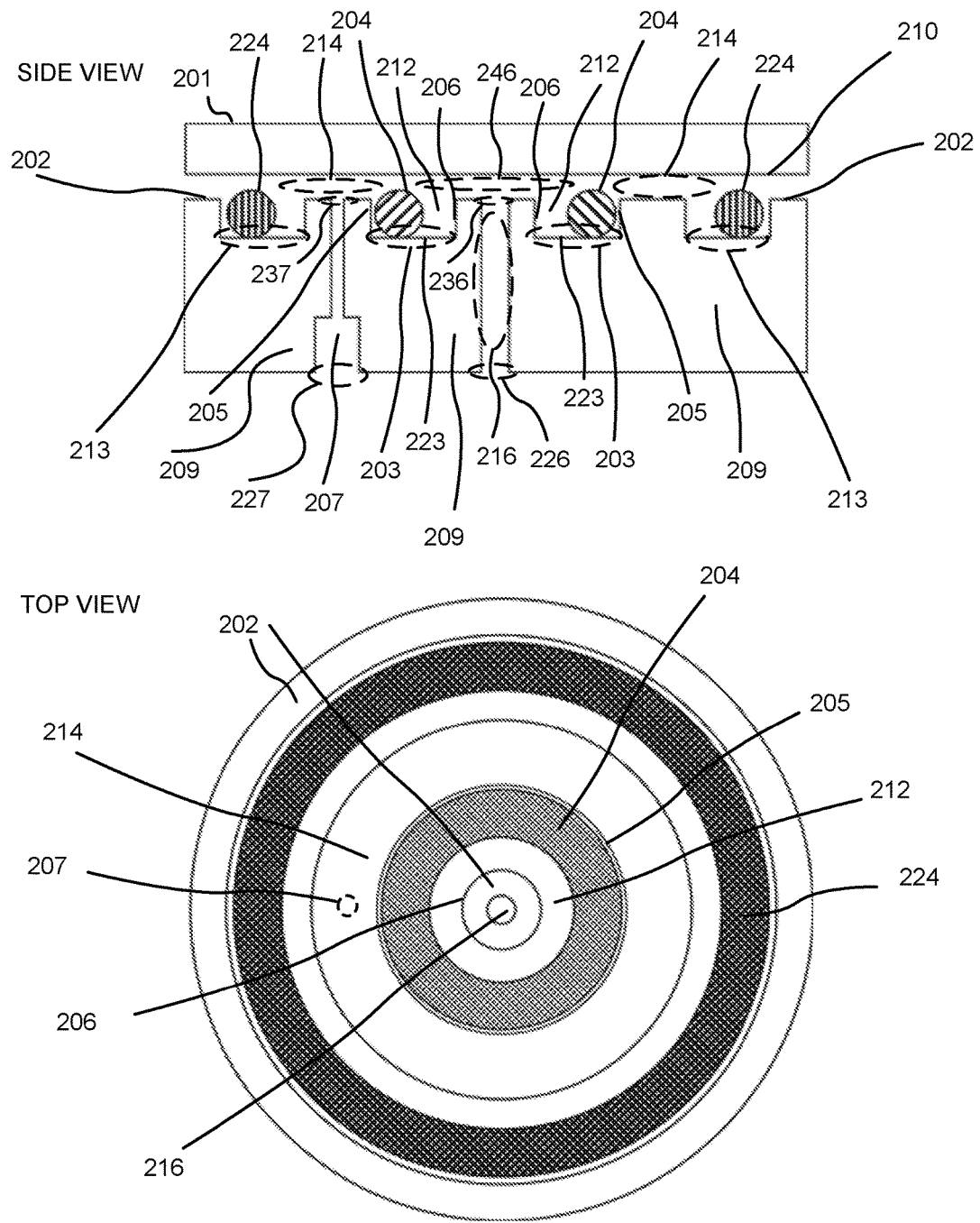
FIG. 2 is a cutaway view of an embodiment of the present invention comprising a seal wash port and dual o-ring system for removing sample from the measurement area of the cell.

Consider the inventive measurement cell setup shown in FIG. 2. In this embodiment the main sealing o-ring 204, in a first o-ring groove 203, having a first o-ring groove bottom surface 223, in a top manifold surface 202 of a manifold 209, covered by a top plate 201 that has a bottom planar surface 210, is left unchanged, including the designed in dead volume 212, which accommodates expansion and tolerance. The difference is that there is a second o-ring 224 and corresponding second o-ring groove 213 outside the first o-ring groove 203. The second o-ring 224 does not participate in sealing the sample containing region 216 within the circumference of the first o-ring groove 203, where the sample containing region 216 includes a sample containing region inlet 226 at the bottom of the sample containing region 216 and a sample containing region outlet 236 at the top of the sample containing region 216, where first o-ring 204, bottom planar surface 210, top manifold surface 202, and sample containing region outlet 236 define a sample overflow region 246. However, if the seal wash region 214 between the two o-rings 204 and 224 is pressurized with an external pressure source through said seal wash port 207, having a seal wash port inlet 227 at the bottom of seal wash port 207 and a seal wash port outlet 237 at the top of seal wash port 207, a force is exerted that moves the inner o-ring 204 against the first o-ring groove inner wall 206 so that the dead volume 212 is outside the sample containing region 216 as desired, where first o-ring 204, second o-ring 224, bottom planar surface 210, top manifold surface 202, and the seal wash port outlet 237 define seal wash region 214.

In many cases it is not convenient, or even possible, to maintain pressure between the two o-rings 204 and 224 because the interior pressure may be high when filling the cell and low only when there is no flow. In this case, one may simply apply pressure alternatively to the interior of the sample containing region 216, which will cause the inner o-ring 204 to slide in its groove 203 to the first o-ring grove outer wall 205, and then apply pressure to the seal wash region 214 between the two o rings 204 and 224 to cause the inner o-ring 204 to push against the inner wall 206. By alternating pressure between the sample containing region 216 and the seal wash region 214, the inner o-ring 204 will wipe the sealing surfaces to expel trapped sample. A plurality of such pressurizations may be applied between each measurement, allowing fresh solvent or sample to dilute and expel any old sample still trapped any dead volume.

Figure 3:
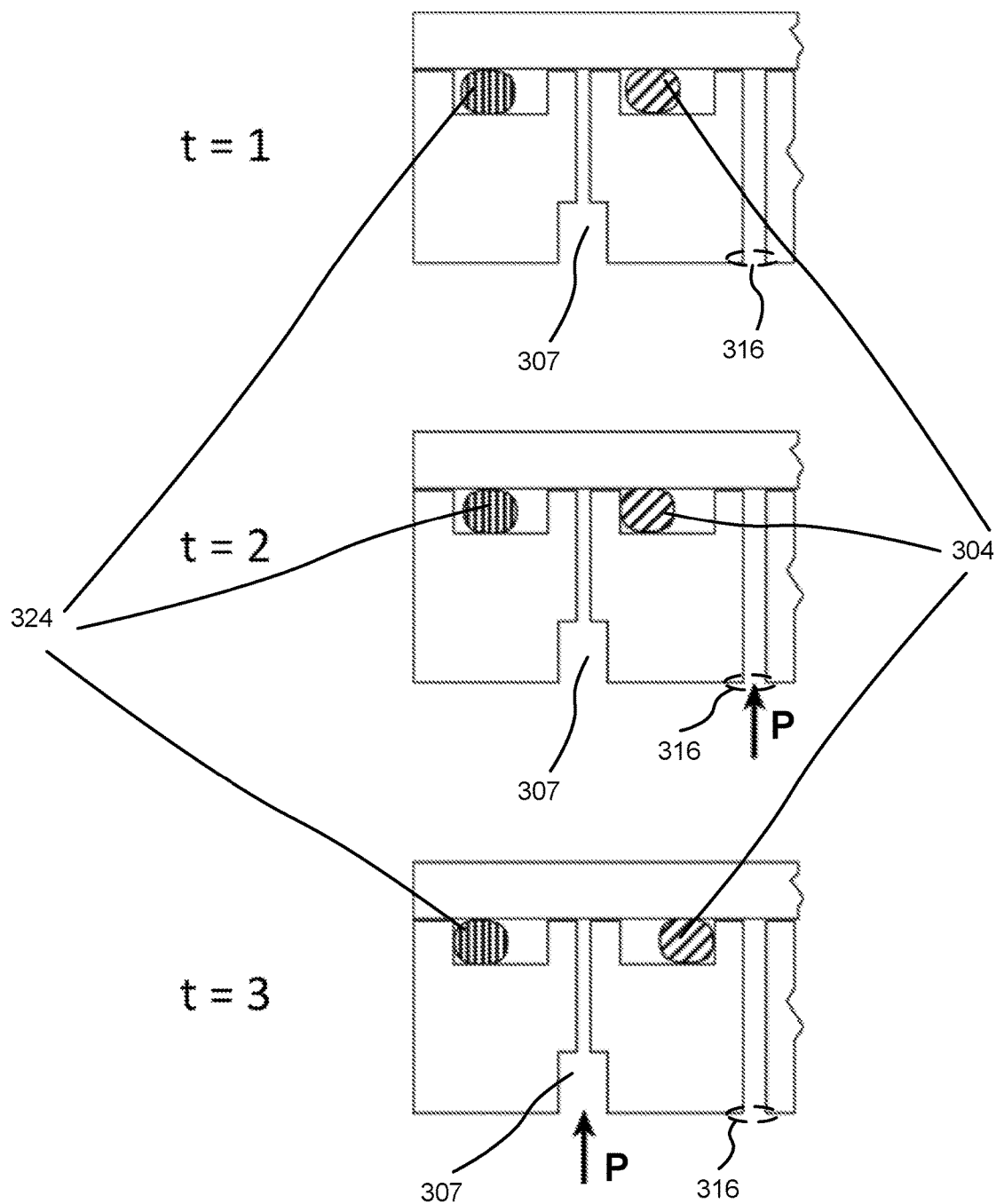
FIG. 3 illustrates an example of the functioning of an embodiment of the present and the positions of the o-rings at various times during the process.

While the space 214 between the two o-rings 204 and 224 is also dead space, it is not in contact with the measurement volume, and therefore the fluid trapped in this space 214 does not affect the measurement. Additionally this means that there is essentially no restriction on the pressurization media used in this region; therefore the seal wash pressurization fluid may be either a gas or liquid. While the inner o-ring 204 is in contact with the sample, and therefore must be of a high quality selected to minimize any interaction with the sample itself, the outer o-ring 224 is never in contact with the sample, and therefore need not be of similar quality material, meaning, in part, that the overall expense associated with the improved flush system can be minimal. Further, while the outer sealing means 224 has been referred to throughout as an o-ring, this sealing mechanism may be any number of other sealing means, such as a washer, gasket, or properly coated surfaces, so long as the seal which is created is sufficient to prevent leaks from the seal wash region 214 between it and the inner o-ring 204 when pressurized. FIG. 3 shows the likely positions of the inner and outer o-rings at various points in time in the process of measurement and flushing. Prior to making any injection, at t=1, the compressed inner o-ring 304 will likely be positioned near the outer wall of the inner groove. It should be noted, however, that the present invention is not limited to outer wall hugging o-ring designs. Designs incorporating o-rings that hug the inner wall or walls are also improved by the present invention. Further there it is not necessary that the inner o-ring hug the same wall in its groove as the outer o-ring hugs it its respective groove, nor is it necessary that either o-ring hug a wall at all, though this may be beneficial for ease of assembly of the structure. The outer o-ring 324 is similarly positioned in its groove at time t=1. At time t=2, sample is injected into the measurement cell through injection port 316, thus increasing the pressure applied to the inner o-ring 304, and pushing it further towards the outer wall of its groove. After the measurement is recorded, a pressure is applied to the seal wash port 307 at t=3 by a liquid or gas medium. The pressure forces the inner o-ring towards the inner wall of its groove, while forcing the outer o-ring farther towards the outer wall of the outer groove. With the inner o-ring forced to the inner wall, the old sample is forced out of the measurement cell dead volume, and a new sample or solvent may be injected, flushing out the old sample far more efficiently and completely than have heretofore been possible.

Figure 4:
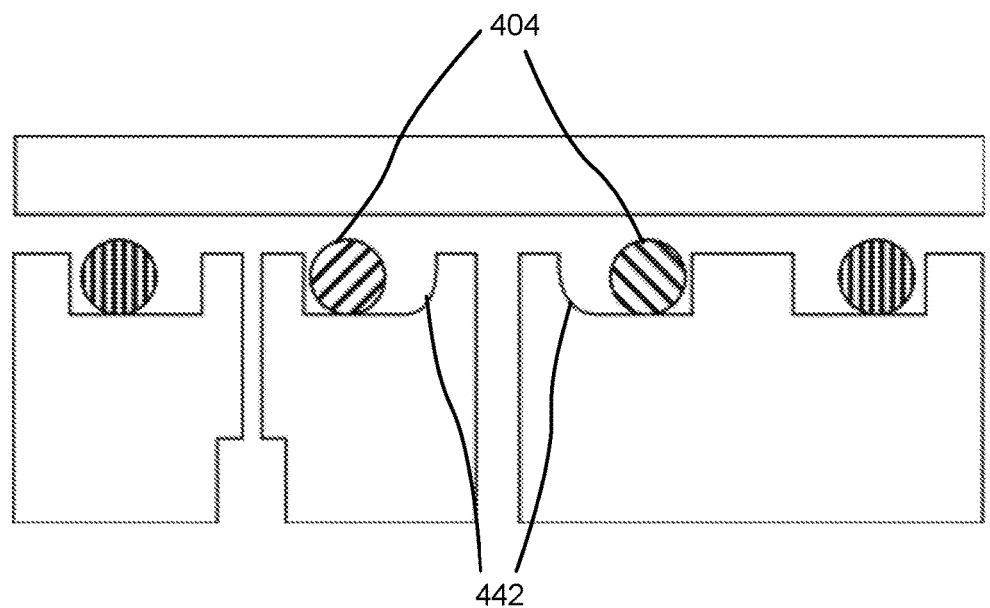
FIG. 4 shows an alternative embodiment of the present invention according to FIG. 3 wherein the inner wall of the inner groove is rounded at the bottom to accommodate the shape of the o-ring and further minimize any sample carried over between injections.

Many variations on the design of the measurement cell are also possible. For example, as illustrated in FIG. 4, the inner o-ring 404 is seated in the inner o-ring groove that may be engineered to have rounded corners 442 to limit, even further, the available dead volume when the inner o-ring 404 is forced to the inner wall in the seal wash step. It should be noted that any of the other walls of either of the grooves may also have rounded corners. The material of which a measurement cell manifold or window is made can also vary. Any substances which allow for the required measurements, for example transparent windows for optical measurements, and which are rigid and strong enough to allow for pressurization of the cell and seal wipe regions without enabling leaks, may be appropriate to practice the present invention. For example, PEEK, stainless steel, polycarbonate resin thermoplastics, and glass are among materials appropriate for use as windows and/or manifolds for the practicing the present invention.

Figure 5:
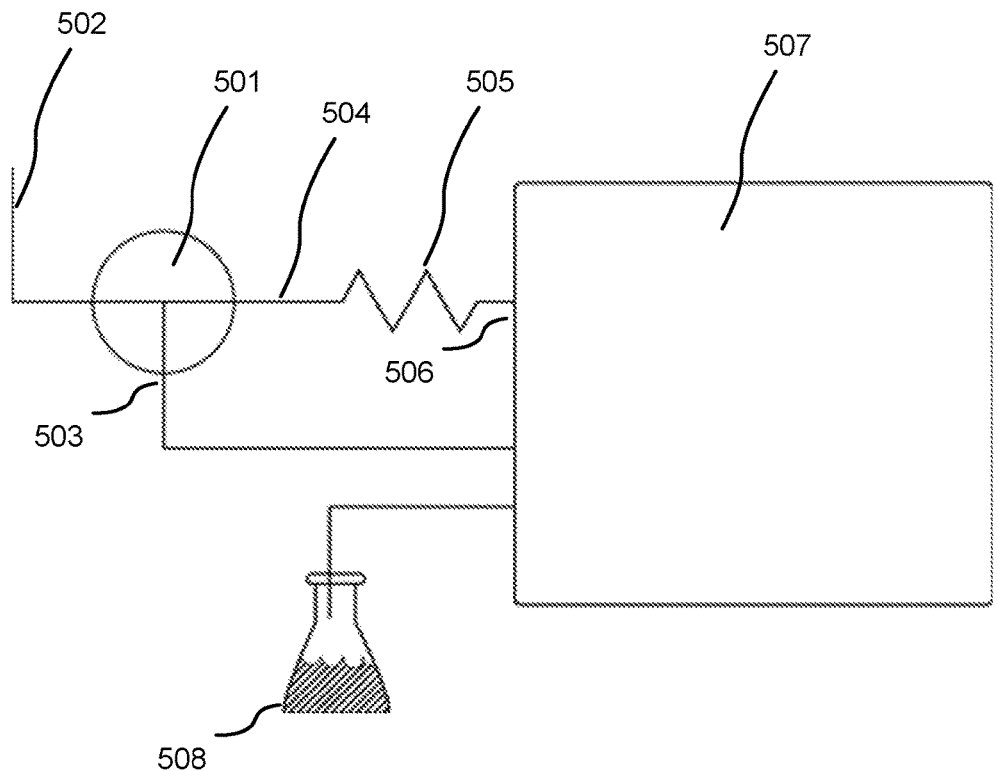
FIG. 5 shows an embodiment of the present invention that makes use of a passive design, wherein a high pressure relative to the measurement area of the cell is maintained in the seal wash area between the two o-rings by means of a restricting capillary tube.

While the above discussion has concerned itself with an active design wherein the ports are generally pressurized by flow controlled with valves, is also possible to provide similar benefits with a passive embodiment of the present invention, as shown in FIG. 5. Instead of injecting directly into the cell, an inline T-union 501 is connected to the sample source tubing 502. One port is connected to the seal wash 503 and the third port 504 is connected to a restriction capillary 505 that then connects to the instrument inlet 506. This way, whenever there is flow, a pressure drop develops across the capillary 505 causing the seal wash port to have a higher pressure than the interior of the cell within the instrument 507. This pressure will force the inner o-ring to the inside of the groove. When the flow is stopped the pressure drops to ambient, and the o-ring stays against the inside wall of the groove. If the system is subsequently pressurized with a pressurization means, the inner o-ring will have very little pressure across it as both sides are pressurized equally. While there may be a transient pressure that forces the inner o-ring back to the exterior of the groove, this will only fill the dead volume with fresh sample, which will get flushed to waste 508 when the next sample is introduced.

Consider now the data collected from a conventional measurement cell not incorporating the present invention presented in FIG. 6. In this experiment a 500 µL sample of a high salt solution of 500 mM KCl was injected into the conventional flow through measurement cell of an electrophoretic mobility measurement instrument (Möbiuζ, Wyatt Technology Corporation, Santa Barbara, Calif.). Once thermal equilibrium was reached in the cell, the conductivity of the sample was measured by the instrument ten times in succession at ten second intervals. The cell was kept under 10 bars of pressure by means of an output restrictor connected to the outlet of the flow through cell. After the initial set of 10 measurements, the cell was flushed with 500 µL, approximately 3 times the cell volume, of deionized water at a flow rate of 250 µL/min. At this point the pump was turned off, thermal equilibrium was established, and an additional 10 measurements were made. After this the cell was again flushed with 500 µL of deionized water flowing at 250 µL/min, and ten further conductivity measurements made. This procedure was repeated several times to generate the data shown in FIG. 6. Each grouping of data points represents one series of 10 measurements. Note how, beginning with the second measurement set (the initial set being a measurement of the sample, and the second measurement being the first post-flush measurement) the very first data point indicates the lowest conductivity of the data set. Subsequent to the first measurement, in a given set, the conductivity rises as residual sample from the original injection trapped within various recesses in the cell are released, causing the conductivity to rise through time with each subsequent measurement within the set as the concentration of ions remaining in the cell equilibrates. Further, note how it is not until the $9^{th}$ attempt at flushing that the final residual sample within the cell has been adequately flushed such that the conductivity has dropped below 1% of the original measured value. Even after 19 attempts at flushing, it never reaches 0.1% of the original value.

Now consider the data presented in FIG. 7. By contrast, this data was collected using a flow through cell modified according to the present invention and used within the same electrophoretic mobility instrument as the data presented in FIG. 6. The process of experimentation was similar to that used to generate the data of FIG. 6 with the exception being that during each flush step four 20 bar pressure pulses were applied to the seal wash region between the two o-rings of the inventive cell embodiment at 30 second intervals. Thus, in each flush stage, the inner o-ring flexes four times and aids in pushing out trapped liquid which would have remained to contaminate the cell with carryover solution from the initial sample injection. Note how, with the inventive cell modification and inventive method, the contamination drops to well below 1% of the original conductivity measurement after only the second flush/pressurization series. After repeated flushing and pressurization combinations the carryover is reduced to below 0.1% even after the cell has equilibrated.

It should be further noted that the residual carryover that is evident in the above experiments even with a cell modified according to the current invention maybe further minimized by improvements to the geometry of the cell design. For example, the inner o-ring groove employed in the cell used to generate the data of FIG. 7 had squared corners, such as those shown in FIG. 2. Angled or rounded corners in the groove, as exhibited in FIG. 4 may further reduce any carryover. Other improvements include utilizing a material with a more polished, less porous, and/or smooth surface or specialized o-rings might minimize any nooks or other available spaces within which injected sample may be trapped.

Further, while the above examples and corresponding figures represent data taken within an electrophoretic mobility measurement cell, as discussed previously, the present invention should in no way be limited in application to electrophoretic mobility measurements. The inventive methods and apparatuses disclosed herein may be equally advantageous to other applications wherein pressure may be applied to the measurement cell, and wherein sample carryover is sought to be reduced, including, but not limited to, light scattering measurements, refractive index detection, UV absorption detection, and viscosity measurements. Further, while the drawings presented herein and much of the discussion above represent the measurement chamber as the region subtended by the inner o-ring, the invention is not limited to such embodiments. Indeed it is possible for the outer region to comprise the measurement cell, e.g. the region between the outer o-ring and the inner o-ring, and the inner region may act as a seal wash. Further, it is possible, in such a configuration, for there to be an additional seal wash region outside of the outer o-ring which may be pressurized and that region, being contained by a third o-ring, also acting as a seal wash.

As will be evident to those skilled in the arts of analytical instrumentation, there are many obvious variations of the methods and devices of our invention that do not depart from the fundamental elements that we have listed for their practice; all such variations are but obvious implementations of the invention described hereinbefore and are included by reference to the claims, which follow.

What is claimed is:

1. A measurement cell comprising:
 a top plate comprising a bottom planar surface;

a manifold comprising
  a top manifold surface,
  a first o-ring groove in the top manifold surface comprising
    a first o-ring groove inner wall,
    a first o-ring groove outer wall, and
    a first o-ring groove bottom surface,
  a second o-ring groove in the top manifold surface and located radially outward from the first o-ring groove,
  a sample containing region within the circumference of the first o-ring groove, wherein the sample containing region comprises a sample containing region inlet at the bottom of the sample containing region and a sample containing region outlet at the top of the sample containing region, and
  a seal wash port between the first o-ring groove and the second o-ring groove, wherein the seal wash port comprises a seal wash port inlet at the bottom of the seal wash port and a seal wash port outlet at the top of the seal wash port;
a first o-ring seated in the first o-ring groove and in contact with the bottom planar surface and in contact with the first o-ring groove bottom surface;
a second o-ring seated in the second o-ring groove;
wherein the first o-ring, the bottom planar surface, the top manifold surface, and the sample containing region outlet define a sample overflow region;
wherein the sample containing region is configured to receive a fluid sample through the sample containing region inlet and is configured to flow the fluid sample through the sample containing region outlet into the sample overflow region, such that the fluid sample exerts pressure on the first o-ring such that the first o-ring impinges on the first o-ring groove outer wall, thereby allowing the fluid sample to enter a dead volume defined by the first o-ring, the bottom planar surface, the first o-ring groove inner wall, and the first o-ring groove bottom surface;
wherein the first o-ring, the second o-ring, the bottom planar surface, the top manifold surface, and the seal wash port outlet define a seal wash region;
wherein the seal wash port is configured to receive a fluid through the seal wash port inlet and is configured to flow the fluid through the seal wash port outlet into the seal wash region, such that the fluid exerts pressure on the first o-ring such that the first o-ring impinges on the first o-ring groove inner wall, thereby expelling the fluid sample from the dead volume.

2. The measurement cell of claim 1 wherein one or more corners contained within the first o-ring groove are rounded.

3. The measurement cell of claim 1 wherein the measurement cell is material selected from the group consisting of stainless steel and polyether ether ketone.

* * * * *